United States Patent [19]

McDonald

[11] Patent Number: 4,834,748

[45] Date of Patent: May 30, 1989

[54] METHOD AND APPARATUS FOR REMOVING CORNEAL TISSUE

[75] Inventor: Marguerite B. McDonald, New Orleans, La.

[73] Assignee: Allergan, Inc., Irvine, Calif.

[21] Appl. No.: 102,344

[22] Filed: Sep. 29, 1987

[51] Int. Cl.$^4$ .......................... A61F 2/14; A61F 17/32; A61B 17/00

[52] U.S. Cl. ........................................ 623/5; 128/305; 128/355; 51/206 R

[58] Field of Search ......................................... 623/4–6; 128/304, 305, 310, 355, 92 VJ; 51/71, 72 R, 73 R, 206 R, 206 P, 206.4

[56] References Cited

U.S. PATENT DOCUMENTS

| | | | |
|---|---|---|---|
| 2,076,449 | 4/1937 | Doner | 51/206 R |
| 3,468,079 | 9/1969 | Kaufman | 128/355 X |
| 3,667,456 | 6/1972 | Charnley | 128/305 X |
| 4,338,748 | 7/1982 | Elbel | 51/206 R |
| 4,346,482 | 8/1982 | Tennant et al. | 128/305 X |

OTHER PUBLICATIONS

Improved Instruments for Hip Arthroplasty, Broomhead's Improved *Smith-Petersen's Reamers*, p. 12 Advertisement–Journal of Bone & Joint Surgery, Nov. 1951.

Refractive Keratoplasty, Reshaping the Eye for Better Sight, by George O. Waring III; Resident & Staff Physician, May 1985, pp. 25–33.

*Primary Examiner*—Ronald L. Frinks
*Attorney, Agent, or Firm*—Gordon L. Peterson

[57] ABSTRACT

Corneal tissue and, in particular, Bowman's membrane is removed by abrading an annular zone of the cornea. The corneal tissue is abraded by rotating an abrading tool having an annular abrading surface in contact with the cornea. A corneal onlay can be attached to the abraded zone of the cornea.

15 Claims, 1 Drawing Sheet

U.S. Patent     May 30, 1989     4,834,748
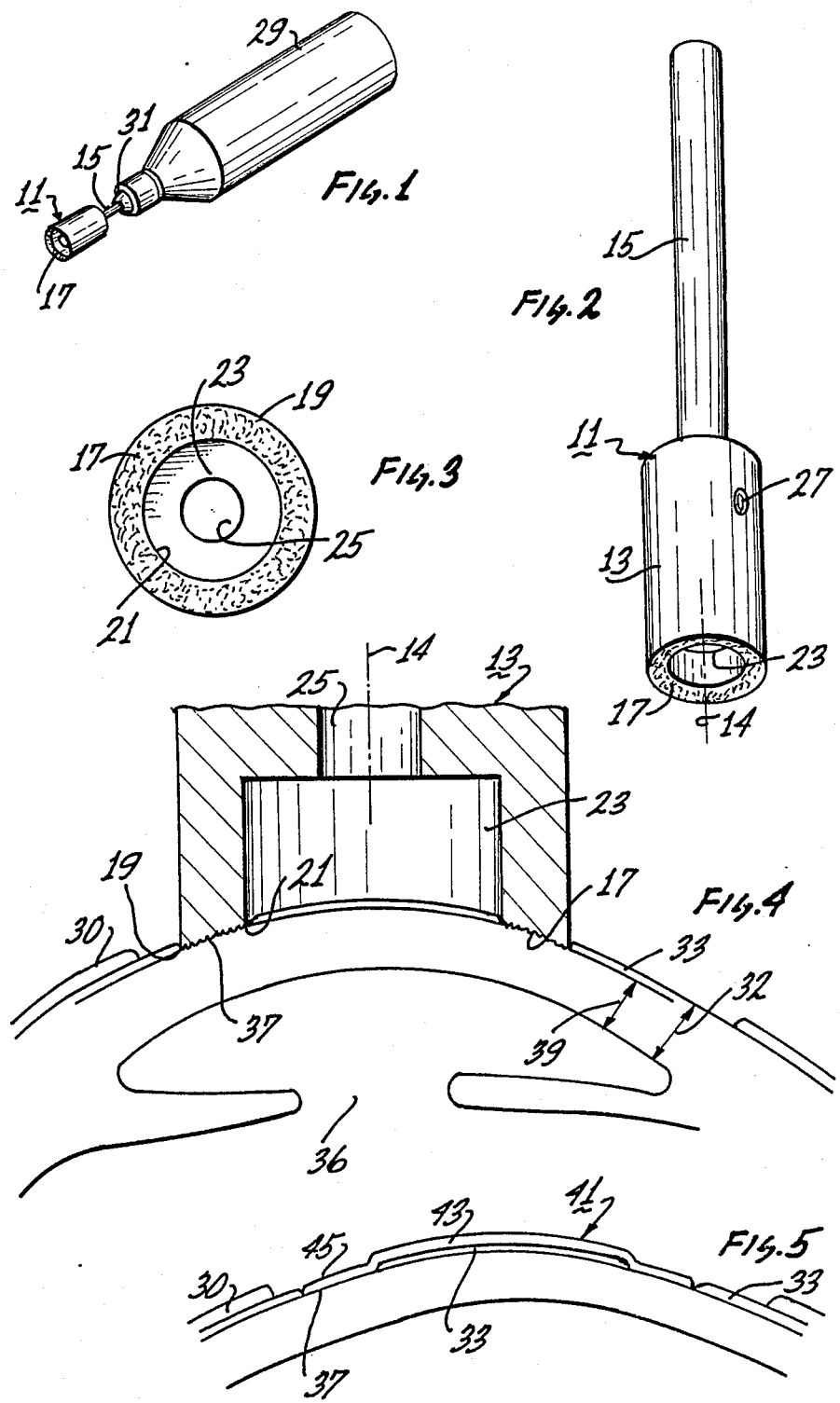

METHOD AND APPARATUS FOR REMOVING CORNEAL TISSUE

BACKGROUND OF THE INVENTION

In one form of corrective eye surgery known as an epikeratophakia procedure, a corneal onlay is attached to the cornea. A corneal onlay typically comprises a central optic and an annular wing, and the wing is attached to the cornea with the optic coaxial with the optical axis of the eye.

The cornea comprises five layers, including an outer layer of epithelial cells, Bowman's membrane immediately posterior of the cells and stroma immediately posterior of Bowman's membrane. In order to properly attach the corneal onlay to the cornea, it is necessary to appropriately prepare the region of the cornea to which the wing is to be attached.

One prior art technique for accomplishing this includes removing the layer of epithelial cells and then removing a wedge-shaped annulus from Bowman's membrane and the underlying stroma. An incision is then made from the posterior end of the resulting groove radially outwardly in an annular zone to define a flap. The wing is inserted beneath the flap. For example, the wedge-shaped annulus may be cut with a trephine, and the incision may be made with a knife. The corneal onlay is attached by inserting the wing beneath the corneal flap and fixing it in place.

One problem with this technique is that it is quite invasive in that an annulus of the cornea must be entirely removed and then the cornea must be cut. In addition, the fixing of the wings beneath the corneal flaps can distort the optic and provide consequent optical distortion for the patient.

A similar prior art technique employs an annular trephine cut through Bowman's membrane and some stroma followed by a radial and circumferential knife cut from the posterior end of the trephine cut to again form a corneal flap. The corneal onlay is attached by inserting the wing on the onlay beneath the corneal flap. This technique is somewhat less invasive but does not solve the optical distortion problem referred to above.

SUMMARY OF THE INVENTION

This invention provides a method and apparatus which generally overcomes the problems identified above. With this invention, a cornea is prepared for a corneal onlay in a less invasive manner than the prior art techniques discussed above. In addition, the wing of the corneal onlay is attached to the cornea in a way which significantly reduces or eliminates the optical distortion problem discussed above.

With this invention, a region of Bowman's membrane is abraded to form an abraded zone of the cornea. The wing of the corneal onlay is then attached to the abraded zone.

This technique affords a number of advantages. For example, the abrasion of the cornea is less invasive than the prior art techniques. The abrasion can be part way or all the way through Bowman's membrane, and if desired, the abrasion may also be into the stroma. In any event, the abrasion does not provide a corneal flap but does provide an abraded zone to which the wing of the corneal implant can be readily attached with sutures or the like until a scar is formed that naturally attaches the corneal onlay to the cornea. Because the corneal flap has been eliminated, the tendency of the corneal flap to distort the optic, and hence the optical properties of the onlay, is also eliminated.

For better attachment, the abraded zone is preferably annular, although this is not required. Although the abrading step can be carried out with different abrading tools, it is preferred to use an abrading tool with an annular abrading surface and to rotate the abrading tool with the abrading surface in contact with the cornea. Rotation may be very rapid, as for example forty thousand rpm, or, if desired, may be carried out manually and slowly. In either event, the rotation of the abrading surface may cause some of the corneal tissue to attach to the abrading surface to reduce its roughness and abrading ability. If desired, the abrading of the corneal tissue can be terminated when the abrading ability of the abrading surface is substantially reduced.

The abrading tool can advantageously include a body having an axis and a distal end and means for defining the abrading surface essentially at the distal end. To provide relative evenness in the depth of the abraded zone, the abrading surface is preferably inclined proximally as it extends radially inwardly. To obtain optimum results, the abrading surface is preferably in the form of a segment of a sphere which generally matches the curvature of the cornea. However, for the dimensions involved, an appropriately configured frusto-conical section may also be used for the abrading surface.

The abrading surface must be capable of abrading the cornea as described herein and should be rough. This rough characteristic of the abrading surface can be provided in various different ways, such as by roughening a surface of the body. Preferably, however, the abrading surface is provided by adhering abrasive particles to the body. The abrasive particles may be particles of a gem, such as a diamond or sapphire.

Because the cornea tends to bulge when subjected to a compressive load, the body preferably has a cavity opening axially outwardly and located close to the inner periphery of the annular abrading surface. The cavity provides a space into which the cornea can bulge. If the abrading tool is to be rotated by a motor, it preferably has a shaft coupled to the body coaxial with the body axis. The shaft can then be received in a chuck of a standard drill motor.

The invention, together with additional features and advantages thereof, may best be understood by reference to the following description taken in connection with the accompanying illustrative drawing.

BRIEF DESCRIPTION OF THE DRAWING

FIG. 1 is a perspective view of an abrading tool constructed in accordance with the teachings of this invention and coupled to a handpiece.

FIG. 2 is a perspective view of the abrading tool.

FIG. 3 is an enlarged bottom plan view of the abrading tool.

FIG. 4 is an enlarged axial, sectional view through the abrading tool and illustrating the abrading tool being used to abrade the cornea.

FIG. 5 is a view similar to FIG. 4 with a corneal onlay attached to the cornea.

DESCRIPTION OF THE PREFERRED EMBODIMENT

FIGS. 1 and 2 show an abrading tool 11 for use in abrading corneal tissue. The abrading tool 11 includes a body 13 constructed of a suitable metal or plastic and having an axis 14 and a shaft 15 suitably coupled to the body 13 and coaxial with the body.

There is an abrading surface 17 at a distal end of the body 13. The abrading surface 17 is annular, rough and coaxial with the axis 14 of the body 13.

Although the abrading surface 17 can be formed in different ways, in this embodiment, it includes diamond particles adhered to the distal end of the body 13. As shown in FIGS. 2 and 4, the abrading surface 17 is inclined proximally as it extends radially inwardly. More specifically, in this embodiment, the abrading surface 17 includes a segment of a sphere having a curvature to generally match the curvature of a cornea of a human eye.

The abrading surface 17 is dimensioned so as to be capable of abrading an annulus of the desired size in the cornea. For example, the abrading surface 17 may have an outer circular periphery or perimeter 19 with a diameter no greater than about the maximum diameter of the cornea, i.e., 11 or 12 millimeters, and preferably no greater than about 9 millimeters and an inner circular periphery or perimeter 21 of about 1.5 to 2 millimeters less than the diameter of the outer periphery.

The body 13 also has an axially opening, cylindrical cavity 23 which opens at the inner periphery 21 of the abrading surface 17. The cavity 23 is useful in defining the inner periphery 21 and in providing a space into which the cornea can bulge during use of the abrading tool 11.

If desired, the body 13 may have a central axial bore 25 (FIG. 4) which extends from the cavity 23 to the other end of the body 13. The shaft 15 is received within the bore 25 and is coupled to the body 13 in any suitable manner, such as by a screw 27 (FIG. 2).

In use, the abrading tool 11 must be rotated. This can be accomplished manually, for example, by gripping and rotating the shaft 15. Alternatively, the shaft 15 can be coupled to a handpiece 29 (FIG. 1) by a conventional chuck 31. The handpiece 29 includes a motor (not shown) and may be a conventional apparatus of the type used to drive a drill bit.

Prior to using the abrading tool 11, the epithelial cells 30 of the cornea 32 (FIG. 4) are first removed using conventional techniques, such as scraping, to expose Bowman's membrane 33 (FIG. 4) of the cornea. Next, the abrading tool 11 is positioned to bring the abrading surface 17 into contact with Bowman's membrane 33, with the axis 14 of the body 13 being generally coaxial with the optical axis of the eye and centered on the pupil 36. The abrading tool 11 is then rotated, and if desired, the motor of the handpiece 29 may rotate the abrading tool at high velocity, such as at least about 5,000 revolutions per minute and, if desired, at least 40,000 rpm. This causes the abrading surface 17 to provide an annular abraded zone 37 in Bowman's membrane 33. The abrasive rotating action is preferably carried out until the abraded zone 37 extends completely through Bowman's membrane 33, although the abrading action can be stopped before Bowman's membrane is completely cut through or after some stroma 39 of the cornea 31, which underlies Bowman's membrane 33, has been removed. If the cornea bulges during this procedure, it can bulge into the cavity 23. As the abrasive action continues, some of the corneal tissue being removed attaches to the abrading surface 17 to reduce its roughness and abrading ability. The abrading of the cornea 32 may be terminated when the abrading ability of the abrading surface 17 is substantially reduced and the abrading surface 17 cleaned to permit additional abrading of the corneal tissue, if desired.

A corneal onlay or epikeratophakia lenticule 41 (FIG. 5) is then attached to the abraded zone 37. The corneal onlay 41, which may be conventional, comprises a circular optic 43 and an annular wing 45 surrounding the optic. The onlay 41 is placed over the cornea as shown in FIG. 5, with the optic 43 being coaxial with the optical axis of the eye and with the annular wing 45 being received in the annular abraded zone 37. In order for this to occur, the abraded zone 37 must be sized to accommodate the wing 45, and preferably, the radial distance between the peripheries 19 and 21 of the abrading surface 17 are approximately equal to the radial distance between the inner and outer peripheries of the annular abraded zone 37. The epithelial cells 30 grow back over the onlay 41.

The wing 45 can be attached to the cornea by sutures (not shown) in FIG. 5 until the body forms a scar to naturally attach the onlay 41 to the cornea. During the healing process, the epithelial cells 30 grow over Bowman's membrane 33.

Although an exemplary embodiment of the invention has been shown and described, many changes, modifications and substitutions may be made by one having ordinary skill in the art without necessarily departing from the spirit and scope of this invention.

I claim:

1. A method of attaching a corneal onlay to the cornea comprising:
   abrading a region of Bowman's membrane of the cornea to provide an abraded zone of the cornea; and
   attaching a corneal onlay to said abraded zone.

2. A method as defined in claim 1 wherein said step of abrading renders said abraded zone annular.

3. A method as defined in claim 1 including providing an abrading tool having an annular abrading surface and said step of abrading includes rotating the abrading tool with the abrading surface in contact with Bowman's membrane.

4. A method as defined in claim 3 wherein said step of rotating includes rotating the abrading tool at least about five thousand rpm.

5. A method as defined in claim 3 wherein said step of providing includes providing the abrading surface generally in the form of a segment of a sphere which generally matches the curvature of the cornea.

6. A method as defined in claim 3 wherein said step of providing includes providing the abrading surface generally in the form of a frusto-conical section.

7. A method as defined in claim 3 wherein the abrading surface is relatively rough, said step of rotating causes the abrading surface to abrade corneal tissue with at least some of said tissue attaching to the abrading surface to reduce its roughness and abrading ability and terminating said step of abrading when the abrading ability of the abrading surface is substantially reduced.

8. An abrading tool for use in abrading corneal tissue comprising:
   a body having an axis and a distal end;
   means defining an abrading surface essentially at said distal end of said body, said abrading surface being relatively rough and being of generally annular configuration about said axis;
   said abrading surface being inclined proximally as it extends radially inwardly; and said abrading surface including a segment of a sphere having a curvature to generally match the curvature of a cornea of a human eye.

9. An abrading tool as defined in claim 8 wherein said body has an axially opening cavity adjacent the inner periphery of the annular abrading surface.

10. An abrading tool as defined in claim 8 including a shaft coupled to said body and having an axis coaxial with the axis of the body.

11. An abrading tool as defined in claim 8 wherein said means defining the abrading surface includes abrasive particles adhered to said body.

12. An abrading tool as defined in claim 11 wherein said body has an axially opening cavity adjacent the inner periphery of the annular abrading surface.

13. An abrading tool for use in abrading corneal tissue comprising:

a body having an axis and a distal end;

means defining an abrading surface essentially at said distal end of said body, said abrading surface being relatively rough and being of generally annular configuration about said axis;

said abrading surface being inclined proximally as it extends radially inwardly; and said abrading surface having an outer circular periphery of no more than about twelve millimeters and an inner circular periphery of about 1.5 to two millimeters less than the diameter of the outer periphery.

14. An abrading tool as defined in claim 13 wherein said abrading surface includes a frusto-conical section.

15. An abrading tool as defined in claim 13 wherein the abrading surface includes a segment of a sphere having a curvature to generally match the curvature of a cornea of a human eye.

* * * * *